United States Patent [19]

Brouwer et al.

[11] Patent Number: 4,927,451
[45] Date of Patent: May 22, 1990

[54] 3-ARYLDIHYDROURACILS

[75] Inventors: Walter G. Brouwer, Guelph, Ontario; Ethel Ellen Felauer, Puslinch, Ontario, both of Canada; Allyn Roy Bell, Cheshire, Conn.

[73] Assignees: Uniroyal Chemical Company, Inc., Middlebury, Conn.; Uniroyal Chemical Ltd/Ltee, Don Mills, Canada

[21] Appl. No.: 292,088

[22] Filed: Dec. 30, 1988

[51] Int. Cl.$^5$ ............... A01N 43/54; C07D 239/22
[52] U.S. Cl. ........................... 71/92; 544/309; 544/314
[58] Field of Search ............... 544/309, 314; 71/92

[56] References Cited

U.S. PATENT DOCUMENTS

| | | | |
|---|---|---|---|
| 4,266,056 | 5/1981 | Henrick et al. | 544/309 |
| 4,329,239 | 5/1982 | Chou | 544/309 |
| 4,338,318 | 7/1982 | Henrick et al. | 544/309 |
| 4,440,928 | 4/1984 | Matsui et al. | 544/309 |
| 4,625,028 | 11/1986 | Smith | 544/309 |
| 4,812,164 | 3/1989 | Wenger et al. | 544/309 |

FOREIGN PATENT DOCUMENTS

| | | | |
|---|---|---|---|
| 103436 | 3/1984 | European Pat. Off. | 544/309 |
| 0195346 | 9/1986 | European Pat. Off. | |
| 0260621 | 3/1988 | European Pat. Off. | |
| 1000803 | 8/1965 | United Kingdom | 544/309 |
| 2021098 | 11/1979 | United Kingdom | 544/309 |

OTHER PUBLICATIONS

Richter et al., Chem. Abst. 75-48734 (1971).
Zeeh et al., Chem. Abst. 75-98338n (1971).
Richter et al., Chem. Abst. 78-71571h (1973).
Zeeh et al., Chem. Abst. 78-71717k (1973).
Badische Anilin-und Soda-Fabrik A-G, Chem. Abst. 79-66048j (1973).
Teranishi et al., Chem. Abst. 92-198131j (1980).
Nakatani et al., Chem. Abst. 100-120950q (1984).
Wenger et al., CA106-50241g, "3-Aryluratils and their use as Herbicides" Mar., Advanced Organic Chemistry, 3rd Edition, p. 689.

*Primary Examiner*—Cecilia Shen
*Attorney, Agent, or Firm*—Glenn E. Karta

[57] ABSTRACT

A compound having the structural formula

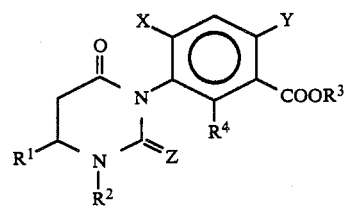

where $R^1$ is hydrogen, $C_1$–$C_4$ alkyl, $C_3$–$C_6$ cycloalkyl, $C_3$–$C_4$ alkenyl or trifluoromethyl; $R^2$ is $C_1$–$C_4$ alkyl, $C_3$–$C_6$ cycloalkyl, $C_3$—$C_4$ alkenyl, $C_7$–$C_{10}$ aralkyl or $C_7$–$C_{10}$ haloaralkyl; $R^3$ is hydrogen or $C_1$–$C_4$ alkyl; $R^4$ is hydrogen or $C_1$–$C_2$ alkyl; X is halogen; Y is hydrogen, $C_1$–$C_4$ alkyl or halogen; and Z is oxygen or sulfur is disclosed. In addition, a process for forming the compound is set forth. A method for controlling weeds which comprises applying a herbicidally effective amount of the compound recited above is also described. Finally, a composition, useful as a herbicide, including the compound of this invention and a suitable carrier therefor is taught.

9 Claims, No Drawings

3-ARYLDIHYDROURACILS

BACKGROUND OF THE INVENTION

1. Field of the Invention

The present invention is directed to a new class of 3-aryldihydrouracils. More specifically, the present invention is directed to a class of 3-aryldihydrouracils having utility as pre- and post-emergent herbicides.

2. Background of the Prior Art

Weeds and other undesirable plants undermine the production of useful agricultural crops by inhibiting the production of foliage, fruit or seeds of these useful plants Weeds cause this undesirable result because of their sharing available light, moisture, nutrients and space with useful crops. Indeed, in many cases weeds exclude light, moisture, nutrients and even space to the useful crops with which they interfere. As a result, the presence of weeds not only reduces the quantity and quality of harvested agricultural crops but, in addition, reduces harvesting efficiency. Thus, it is not surprising that weed control is essential for the successful and economic production of many agronomic and horticultural crops including corn (*Zea mays* L.), cotton (*Gossypium hirsutum* L.) and peanuts (*Archis hypogaea* L.).

In addition to the economic necessity of controlling weeds, to ensure efficient production of useful crops, the control of weeds on noncropped areas is also essential. Weeds present a fire hazard. Many weeds give off pollen which cause serious irritation and illness to a significant percentage of the population afflicted with allergies. Moreover, weeds can cause undesirable drifting of sand, snow and the like. Therefore, suppression of undesirable weed growth is not only advantageous in the case of the successful growth of useful crops but, also, is useful even on lands on which useful crops are not grown. For these reasons, although a large number of compounds possessing herbicidal activity are known, there is a continuing need in the art for the identification and use of new and effective additional compounds to control the growth of unwanted vegetation.

Substituted 3-aryluracils are known in the art. Indeed, substituted 3-aryluracils are disclosed as possessing herbicidal activity. European Patent Application Nos. 0195 346 A2 and 0 260 621 A2, both to Wenger et al., disclose two classes of 3-aryluracils useful as herbicidal agents. The compounds of the '346 and '621 applications are uracil compounds, that is, aromatic heterocyclic compounds substituted at the 3-position with substituted phenyl groups. These compounds are structurally removed from aryl substituted saturated heterocyclic compounds.

The above remarks establish the continuing need in the art to develop new and improved herbicides to control undesired vegetation that interferes with the successful production of useful plants as well as negating other adverse effects associated with the uncontrolled growth of weeds and the like. These remarks also establish that the class of compounds, saturated heterocyclic dihydrouracils substituted at the 3-position with substituted aryl represent a class of compounds not known in the art.

SUMMARY OF THE INVENTION

A new class of compounds, benzoate-substituted dihydrouracil derivatives, has now been discovered. These compounds have been found to possess excellent herbicidal activity. This activity is manifested in both pre- and post-emergent applications. That is, the class of compounds of the present invention effectively controls undesired vegetation prior to and after emergence from the soil.

In accordance with the present invention a new class of compounds having the structural formula

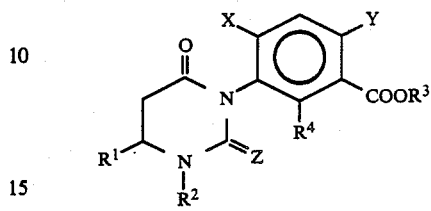

where $R^1$ is hydrogen, $C_1-C_4$ alkyl, $C_3-C_6$ cycloalkyl, $C_3-C_4$ alkenyl, or trifluoromethyl; $R^2$ is $C_1-C_4$ alkyl, $C_3-C_6$ cycloalkyl, $C_3-C_4$ alkenyl, $C_7-C_{10}$ aralkyl or $C_7-C_{10}$ haloaralkyl; $R^3$ is hydrogen or $C_1-C_4$ alkyl; $R^4$ is hydrogen or $C_1-C_2$ alkyl; X is halogen; Y is hydrogen, $C_1-C_4$ alkyl or halogen; and Z is oxygen or sulfur is taught.

In further accordance with the present invention a process for preparing the above-described class of compounds is disclosed. In this process a urea derivative of the formula

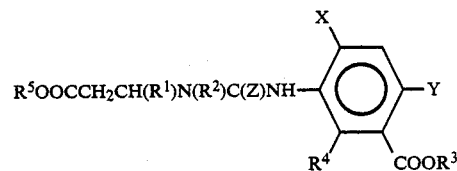

wherein $R^1$, $R^2$, $R^3$, $R^4$, X, Y and Z have the meanings given for the compound of the present invention and $R^5$ is $C_1-C_4$ alkyl, in an alcohol having the structural formula $R^3OH$, is subjected to strong aqueous acid cyclization.

In still further accordance with the present invention a composition comprising the compound of the subject invention, and a suitable carrier therefor is set forth.

In yet still further accordance with the subject invention, a method of controlling weeds and other undesirable vegetation is described. In this method a herbicidally effective amount of the compound of this invention is applied to the locus to be protected.

DETAILED DESCRIPTION

The present invention is directed to a class of compounds having the structural formula

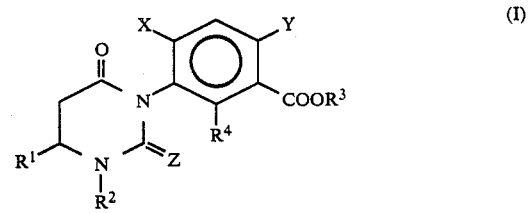

(I)

where $R^1$ is hydrogen, $C_1-C_4$ alkyl, $C_3-C_6$ cycloalkyl, $C_3-C_4$ alkenyl or trifluoromethyl; $R^2$ is $C_1-C_4$ alkyl, $C_3-C_6$ cycloalkyl, $C_3-C_4$ alkenyl, $C_7-C_{10}$ aralkyl or $C_7-C_{10}$ haloaralkyl; $R^3$ is hydrogen or $C_1-C_4$ alkyl; $R^4$ is hydrogen or $C_1$–$C_2$ alkyl; X is halogen; Y is hydrogen, $C_1$–$C_4$ alkyl or halogen; and Z is oxygen or sulfur.

Preferably, the compound of the present invention has the structural formula I where $R^1$ is hydrogen, $C_1$–$C_2$ alkyl or trifluoromethyl; $R^2$ is $C_1$–$C_3$ alkyl, cyclohexyl, propenyl, $C_7$–$C_9$ aralkyl or $C_7$–$C_9$ haloaralkyl; $R^3$ is hydrogen or $C_1$–$C_3$ alkyl; $R^4$ is hydrogen or methyl; X is fluorine; Y is hydrogen, $C_1$–$C_2$ alkyl or chlorine; and Z is oxygen.

More preferably, the compound of the present invention has the structural formula I where $R^1$ is hydrogen, methyl or trifluoromethyl; $R^2$ is methyl, isopropyl, cyclohexyl, propenyl or chlorobenzyl; $R^3$ is hydrogen or isopropyl; $R^4$ is hydrogen; and Y is methyl or chlorine. The meanings of X and Z are those given in the preferred embodiment of the compound of the present invention.

The compound of the present invention, the compound having the structural formula I, where $R^1$, $R^2$, $R^3$, $R^4$, X, Y and Z have the meanings given for the broadest definition of the compound, is prepared in a series of steps which begins with the reaction of a primary amine of the formula

$$R^2NH_2 \qquad (II)$$

where $R^2$ has the same meanings as those given for the compound having the structural formula I and an unsaturated ester of the formula

$$R^1CH=CHCOOR^5 \qquad (III)$$

where $R^1$ has the meanings as those given for the compound having the structural formula I; and $R^5$ is $C_1$–$C_4$ alkyl. In the preferred embodiment wherein $R^1$ has the meanings hydrogen or methyl, an acrylic or a crotonic ester, respectively, is utilized. Of course, other unsaturated esters are employed when $R^4$ has meanings other than hydrogen and methyl.

The product of this reaction of a primary amine and an unsaturated ester is a N-substituted beta-alanine ester having the structural formula

$$R^1(R^2NH)CHCH_2COOR^5 \qquad (IV)$$

wherein $R^1$, $R^2$, $R^5$ have the same meanings as those given for the compounds having the structural formulas I and III.

The beta-alanine ester having the structural formula IV is, in turn, reacted with an isocyanate or isothiocyanate having the structural formula

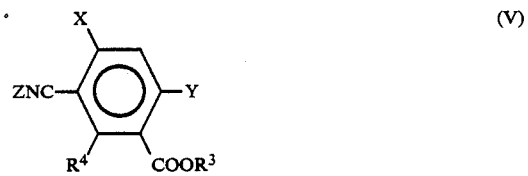

where $R^3$, X, Y and Z have the same meanings as those given for the compound having the structural formula I. The product of reaction between the compound having the structural formula IV, the beta-alanine ester, and the isocyanate or isothiocyanate compound having the structural formula V is a urea derivative having the structural formula

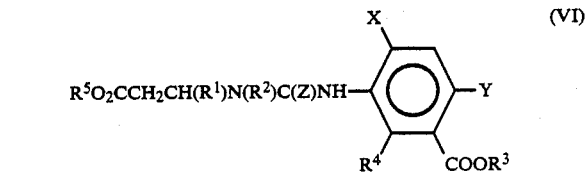

where $R^1$, $R^2$, $R^3$, $R^5$, X, Y and Z have the same meanings as those given for compounds having the structural formulas I and III.

The urea derivative having the structural formula VI is subjected to acid cyclization. That is, the urea derivative having the structural formula VI, in alcoholic solution, is reacted with a strong aqueous acid, preferably hydrochloric acid, to form the compound of the present invention defined by structural formula I. It is important to emphasize that the alcohol utilized in this reaction must have the structural formula $R^3OH$, where $R^3$ has the same meanings as those given for the compound having the structural formula I.

The present invention is also directed to a composition. The composition, having utility as a herbicidal agent, comprises the compound having the structural formula I where $R^1$, $R^2$, $R^3$, $R^4$, X, Y and Z have the meanings given for the broadest definition of the compound having the structural formula I, and a suitable carrier therefor.

Preferably, the composition of the present invention comprises a compound having the structural formula where $R^1$, $R^2$, $R^3$, $R^4$, X, Y and Z have the meanings given for the preferred embodiment of the compound having the structural formula I and a suitable carrier therefor.

More preferably, present invention is directed to a composition comprising a compound having the structural formula I where $R^1$, $R^2$, $R^3$, $R^4$ and Y have the meanings given for the more preferred embodiment of the compound having the structural formula I and where X and Z have the meanings given for the preferred embodiment of the compound having the structural formula I and a suitable carrier therefor.

The principal utility of the composition of the present application are as herbicidal compositions. Therefore, in a preferred embodiment, the concentration of the component of the composition defined by the compound having the structural formula I is a herbicidally effective amount of that compound.

As stated above, the composition of the present application includes, as one component thereof, a carrier suitable for admixture with the active agent of the composition, a compound having the structural formula I. The identity of the carrier is very broad. The carrier may be a finely-divided particulates, granules, pellets, wettable powders, flowable liquids, soluble powders, aqueous or organic solvents, aqueous or organic dispersants or aqueous or organic emulsifying agents.

Among the materials that can be utilized to produce a solid carrier, that is, a carrier in the form of finely-divided particulates, granules, pellets, wettable powders, soluble powders and the like, are such organic and inorganic materials as appapulgite clay, sand, vermiculite, corn cob, activated carbon and mineral silicates. Among the preferred mineral silicates are mica, talc, pyrophyllite, clays and the like.

In the case where the carrier is a solid, a solid composition may be prepared with the active compound impregnated onto the solid carrier. Alternatively, the active compound may be formulated into a wettable powder by grinding it into a fine powder and mixing it with the solid carrier to which a surface active dispersing agent has been added. The wettable powder is then dispersed in water and sprayed onto the soil surface, the crop to be protected and/or the weeds.

The composition may be liquid. A liquid solution is representative of a preferred embodiment of a liquid composition. In the case of a liquid solution, the active compound is dissolved in an aqueous or organic solvent. Among the preferred solvents employed in this invention are aromatic or aliphatic hydrocarbons. Of the hydrocarbons, toluene is particularly preferred.

Of the liquid compositions with the contemplation of this invention, liquid emulsions are more commonly employed than are liquid solutions. An emulsion is preferred because the compound having the structural formula I is an organic compound. Therefore, a composition utilizing the cheapest known carrier, water, is preferred. To provide such a composition the active compound is usually dissolved in an organic solvent to which a surface active dispersing or emulsifying agent is added. Water is then added to form the emulsion. The water emulsion is applied to the locus to be protected, usually by spraying. Alternatively, the emulsion may utilize an organic liquid, such as oil, as the dispersant.

The surface active emulsifying agent may be any one of the many agents known to those skilled in the art. Examples of appropriate surface active agents are provided in McCutcheon's Detergents and Emulsifiers, Allured Publishing Company, Ridgewood, N.J. (1980).

In still another aspect of the present invention, a method for controlling weeds and undesirable vegetation, which comprises applying a herbicidally effective amount of the compound having the structural formula I, where $R^1$, $R^2$, $R^3$, $R^4$, X, Y and Z have the meanings given for the broadest meaning of the compound of this application, to the locus to be protected, is provided.

Preferably, the method of the present invention for controlling weeds comprises applying a herbicidally effective amount of the compound having the structural formula I, where $R^1$, $R^2$, $R^3$, $R^4$, X, Y and Z have the meanings given for the preferred embodiment of the compound having the structural formula I, to the locus to be protected.

More preferably, the method of controlling weeds of the present invention includes the application of a herbicidally effective amount of the compound having the structural formula I, where $R^1$, $R^2$, $R^3$, $R^4$ and Y have the meanings given for the more preferred embodiment of the compound having the structural formula I and X and Z have the meanings given for the preferred embodiment of the compound having the structural formula I, to the locus to be protected.

In a preferred embodiment, the herbicidally effective concentration of the active compound of this application, the compound having the structural formula I, ranges between about 1% to about 95% by weight, based on the total weight of the composition. In the preferred embodiment, wherein the compound having the structural formula I is utilized as an emulsion herbicidal composition, the concentration of the active compound is typically between about 0.002% and about 80% by weight, based on the total weight of the composition.

A herbicidally effective amount of the compound having the structural formula I, in a preferred embodiment of the method of controlling weeds of this invention, typically involves application of from about 0.05 pound to about 25 pounds of the compound having the structural formula I per acre (about 0.056 kilogram to about 28 kilograms per hectare), when the compound is employed as a preemergence herbicide. Application of the preemergence herbicide is typically made to the soil which contain weed and the desired crop seeds. Such application is made either to the surface of the soil or applied 1 to 3 inches (2.5 to 7.5 cm.) under the surface of the soil.

In the event that the method for controlling weeds is undertaken after emergence of the weeds, that is, a method of postemergence herbicidal control is utilized, the amount of the active compound, the compound having the structural formula I, is about 0.05 to about 25 pounds per acre (about 0.056 to about 28 kg/ha). Usually, postemergent application occurs by aerial spraying of the undesired vegetation.

Of course, hard and fast rules regarding concentration of the active compound depends on a multiplicity of factors such as soil type, soil pH, soil organic matter content, the quantity and intensity of rainfall before and after treatment, air and soil temperature, light intensity and light duration per day. All of these factors have an influence of the efficacy of the compound of this invention as a herbicide. Those skilled in the art can, by routine experimentation, readily determine the optimum conditions for employment of the compounds within the contemplation of this invention.

The following examples are given to illustrate the scope of the invention embodied herein. Since these examples are given for illustrative purposes only, the invention should not be interpreted as being limited to the examples recited hereinafter.

EXAMPLE 1

Preparation of 1-Methylethyl 2-chloro-4-fluoro-5-(hexahydro-3,4-dimethyl-2,6-dioxo-1-pyrimidinyl)benzoate (Compound No. 2)

Methanol (200 ml.) was saturated with gaseous methylamine (40 g., 1.3 mole) at 0° C. with stirring. Methyl crotonate (50 g., 0.5 mole) was added, dropwise, to the thus formed methylamine solution. The dropwise addition occurred with stirring at 0° C. Upon completion of the addition of the methyl crotonate, the reaction mixture was left overnight at 20° C. The methanol solvent was driven off leaving a residual oil. The oil was distilled at a temperature of 55° to 62° C. at low pressure (12 mm Hg.) to yield 18 g. of methyl-3-(methylamino)-butanoate.

Methyl 3-(methylamino)butanoate (6.8 g., 0.05 mole), formed in accordance with the above procedure, was stirred in dry diethyl ether (50 ml.) to form a solution which was treated with a solution of 1-methylethyl 2-chloro-4-fluoro-5-isocyanatobenzoate (12.8 g., 0.05 mole) in dry diethyl ether (50 ml.). The latter solution was added dropwise to form a reaction mixture. This reaction mixture was refluxed for one hour. After cooling, the solvent was removed leaving an oil.

The thus formed crude oil was refluxed in a mixture of isopropyl alcohol (50 ml.) and 6N hydrochloric acid (100 ml.) for three hours. The isopropyl alcohol solvent was removed under reduced pressure to yield a crude oil. The oil was passed into methylene chloride, washed with water, dried over magnesium sulfate, filtered and evaporated to yield a residue. The residue was crystallized from isopropyl alcohol resulting in the product, 1-methylethyl 2-chloro-4-fluoro-5-(hexahydro-3,4-dimethyl-2,6-dioxo-1-pyrimidinyl)benzoate. The product, obtained at a yield of 5.6 g., was characterized by a melting point of 105° C. to 107° C.

EXAMPLE 2

Preparation of 1-Methylethyl 2-chloro-4-fluoro-5-[hexahydro-3-(1-methylethyl)-6-oxo-2-thioxo-1-pyrimidinyl]benzoate (Compound No. 11)

A mixture of methyl acrylate (43 g., 0.5 mole) and isopropylamine (25 g., 0.42 mole) in methanol (400 ml.) was left standing overnight at 20° C. The reaction mixture in methanol was then warmed to 60° C. for two hours. The solvent was driven off and the residue distilled to produce 50 g. of methyl N-(1-methylethyl)-beta-alanine ester characterized by a boiling point of 67° C. to 74° C. at a pressure of 12 mm Hg.

The thus formed methyl N-(1-methylethyl)-beta-alanine ester (7.3 g., 0.5 mole) was dissolved in dry tetrahydrofuran (50 ml.). This solution was contacted with a solution of 1-methylethyl 2-chloro-4-fluoro-5-isothiocyanato-benzoate (13.6 g., 0.05 mole) in dry tetrahydrofuran (50 ml.). These reactants, each in tetrahydrofuran solution, were refluxed for 8 hours. The isothiourea product of this reaction was isolated as an oil after the removal of the tetrahydrofuran solvent.

The thus formed isothiourea oil was refluxed in a mixture of 6N hydrochloric acid (100 ml.) and isopropyl alcohol (50 ml.) for two hours. The reaction mixture was diluted with water and the product extracted into methylene chloride. The extract was washed with water, then washed with a saturated solution of sodium bicarbonate, dried over magnesium sulfate, filtered and evaporated to dryness to leave a crude oil. The crude oil was purified by preparative liquid chromatography. The purified product, obtained in a yield of 1.1 g., 1-methylethyl 2-chloro-4-fluoro-5-[hexahydro-3-(1-methylethyl)-6-oxo-2-thioxo-1-pyrimidinyl]-benzoate, was isolated as a viscous oil.

EXAMPLE 3

Preparation of 1-Methylethyl 2-chloro-4-fluoro-5-[hexahydro-3-methyl-2,6-dioxo-4-(trifluoromethyl)-1-pyrimidinyl]benzoate (Compound No. 12)

Gaseous methylamine was bubbled into absolute ethanol (50 ml.) at 0° C. until 8.5 g. (0.27 mole) was dissolved in the ethanol solvent. Ethyl 4,4,4-trifluorocrotonate (25.0 g., 0.15 mole) in ethanol was added to the methylamine solution at 0° C. The reaction mixture in ethanol was left overnight at 20° C. Thereafter, the solvent was driven off and the residue distilled to produce ethyl 3-(methylamino)-4,4,4-trifluorobutanoate in a yield of 22 g. This product was characterized by a boiling point, at a pressure of 12 mm. Hg., of 62° C. to 64° C.

The thus formed ethyl 3-(methylamino)-4,4,4-trifluorobutanoate (10.0 g., 0.05 mole) was dissolved in dry diethyl ether (50 ml.) and treated with a solution of 1-methylethyl 2-chloro-4-fluoro-5-isocyanatobenzoate (12.2 g., 0.05 mole) in dry diethyl ether (50 ml.) and refluxed for two hours. The removal of the diethyl ether solvent left an oil, the urea product of this reaction.

The oil product was refluxed in a mixture of 6N hydrochloric acid (100 ml.) and isopropyl alcohol (50 ml.) for three hours. The mixture was cooled, diluted with water and the product extracted into methylene chloride. The extract was washed with water, then with a saturated solution of sodium bicarbonate, dried over magnesium sulfate, filtered and evaporated. The residue product was recrystallized from isopropyl alcohol to yield 1.9 g. of 1-methylethyl 2-chloro-4-fluoro-5-[hexahydro-3-methyl-2,6-dioxo-6-(trifluoromethyl)-1-pyrimidinyl]benzoate. The product was characterized by a melting point of 142° C. to 143° C.

EXAMPLE 4

Preparation of Compound Nos. 1, 3–10 and 13–16

Compound Nos. 1, 3–10 and 13–16, compounds within the scope of the generic compound of the present invention, were prepared in accordance with the procedures set forth in Examples 1 to 3. These compounds are summarized in Table I. Table I not only defines the compounds but also characterizes these compounds by their melting point when such melting points were obtainable. These compounds also gave satisfactory infrared spectra, and/or NMR spectra, and/or elemental analysis. For completeness, the compounds of Examples 1 to 3, Compound Nos. 2, 11 and 12, respectively, are included in Table I.

TABLE I

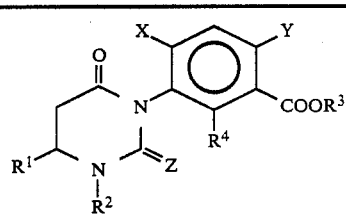

| Cpd. No. | R¹ | R² | R³ | R⁴ | X | Y | Z | M.P., C. |
|---|---|---|---|---|---|---|---|---|
| 1 | H |  | CH(CH₃)₂ | H | F | Cl | O | 139–141 |

TABLE I-continued

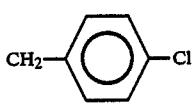

| Cpd. No. | R¹ | R² | R³ | R⁴ | X | Y | Z | M.P., C. |
|---|---|---|---|---|---|---|---|---|
| 2 | CH₃ | CH₃ | CH(CH₃)₂ | H | F | Cl | O | 105–107 |
| 3 | H | CH₂—⟨C₆H₄⟩—Cl | CH(CH₃)₂ | H | F | Cl | O | 88–90 |
| 4 | H | CH₃ | H | H | F | Cl | O | 238–241 |
| 5 | H | CH(CH₃)₂ | H | H | F | Cl | O | 177–179 |
| 6 | H | CH(CH₃)₂ | CH(CH₃)₂ | H | F | Cl | O | oil |
| 7 | CH₃ | CH(CH₃)₂ | CH(CH₃)₂ | H | F | Cl | O | glass |
| 8 | H | CH₃ | CH(CH₃)₂ | H | F | Cl | O | oil |
| 9 | H | CH₂CH=CH₂ | CH(CH₃)₂ | H | F | Cl | O | oil |
| 10 | CF₃ | CH(CH₃)₂ | CH(CH₃)₂ | H | F | Cl | O | oil |
| 11 | H | CH(CH₃)₂ | CH(CH₃)₂ | H | F | Cl | S | oil |
| 12 | CF₃ | CH₃ | CH(CH₃)₂ | H | F | Cl | O | 142–143 |
| 13 | CF₃ | CH₃ | CH(CH₃)₂ | H | F | CH₃ | O | glass |
| 14 | CH₃ | CH₃ | CH(CH₃)₂ | H | F | CH₃ | O | 124–126 |
| 15 | CH₃ | CH₃ | CH(CH₃)₂ | H | F | H | O | 120–122 |
| 16 | CH₃ | CH₃ | CH(CH₃)₂ | CH₃ | F | CH₃ | O | oil |

EXAMPLE 5

Preemergence Control

Three hundred mg. of each of the compounds listed in Table I, Compound Nos. 1–16, were dissolved in acetone (10 ml.). An emulsifying agent, ethoxylated sorbitan monolaureate (30 mg.), was added to each of the thus formed solutions. Stock solutions (3000 ppm) were formed by the addition of distilled water (90 ml.) to each of the 10 ml acetone solutions. Ten ml. of each of the 3,000 ppm stock solutions were diluted to a concentration of 250 ppm by the addition of distilled water.

Each of Compound Nos. 1–16 were tested by drenching 46 ml. of each of the solutions, at a rate of 10 pounds per acre (11.2 kg/ha), onto the surface of soil disposed in 4½ inch (11.25 cm.) plastic pots wherein seeds of the following weeds had been planted: velvet leaf (*Abutilon theophrasti* Medic.) (VL), jimsonweed (*Datura stramonium* L.) (JW), tall morningglory (*Ipomea purpurea* L. Roth) (TM), switchgrass (*Panicum virgatum* L.) (SG), barnyard grass (*Echinolchloa crus-galli* (L.) Beauv.) (BG) green foxtail (*Setaria viridis*) (L.) Beauv.) (GF).

Percent control of each of these weeds was determined two weeks after treatment by comparison with untreated controls. The results of these tests are summarized in Table II. The data in Table II indicates good to excellent herbicidal efficacy exhibited by the compounds of this invention.

TABLE II

| | Preemergence Activity (% Control at 11.2 kg/ha) | | | | | |
|---|---|---|---|---|---|---|
| Cpd. No. | VL | JW | TM | BG | SG | GF |
| 1 | 0 | 0 | 0 | 0 | 0 | 0 |
| 2 | 100 | 100 | 100 | 100 | 100 | 100 |
| 3 | 100 | 90 | 0 | 95 | 90 | 85 |
| 4 | 0 | 0 | 0 | 0 | 50 | 75 |
| 5 | 90 | 95 | 0 | 100 | 70 | 65 |
| 6 | 100 | 60 | 100 | 100 | 100 | 100 |
| 7 | 100 | 0 | 100 | 100 | 100 | 100 |
| 8 | 0 | 0 | 0 | 0 | 0 | 0 |
| 9 | 100 | 0 | 100 | 100 | 100 | 100 |
| 10 | 0 | 0 | 0 | 0 | 0 | 0 |
| 11 | 100 | 0 | 95 | 95 | 100 | 100 |
| 12 | 0 | 0 | 50 | 0 | 30 | 100 |
| 13 | 100 | 100 | 100 | 95 | 90 | 90 |
| 14 | 100 | 100 | 100 | 100 | 100 | 100 |
| 15 | 25 | 0 | 0 | 0 | 90 | 100 |
| 16 | 0 | — | 0 | 0 | 100 | 100 |

EXAMPLE 6

Postemergence Control

To test the effectiveness of the compounds of this invention as postemergence herbicides, a 3,000 ppm solution, prepared in accordance with the procedure described in Example 5, was applied to foliage of each of the weeds enumerated in Example 5. This was accomplished by wetting the foliage of each of the weeds to the drip point with the above-described solutions. The solutions were applied to the foliage as atomized sprays employing a DeVilbiss [trademark] sprayer. The spraying of the weed foliage occurred six days after foliage emergence. Two weeks after the treatment with the compounds after this invention, percent weed control was determined. As in the case of preemergence control, percent weed control was determined by comparison with untreated controls. The results of this test are summarized in Table III.

TABLE III

Postemergence Activity
(% Control at 3000 ppm)

| Cpd. No. | VL | JW | TM | BG | SG | GF |
| --- | --- | --- | --- | --- | --- | --- |
| 1 | 100 | 80 | 100 | 100 | 100 | 100 |
| 2 | 100 | 100 | 100 | 100 | 100 | 100 |
| 3 | 100 | 90 | 95 | 95 | 100 | 100 |
| 4 | 100 | 70 | 100 | 85 | 40 | 45 |
| 5 | 100 | 30 | 75 | 70 | 85 | 35 |
| 6 | 100 | 95 | 100 | 100 | 100 | 90 |
| 7 | 90 | 95 | 60 | 70 | 95 | 35 |
| 8 | 100 | 100 | 100 | 80 | 95 | 85 |
| 9 | 100 | 95 | 100 | 90 | 95 | 90 |
| 10 | 75 | 85 | 65 | 35 | 15 | 15 |
| 11 | 100 | 100 | 100 | 100 | 95 | 90 |
| 12 | 25 | 95 | 95 | 80 | 25 | 75 |
| 13 | 70 | 50 | 75 | 30 | 15 | 35 |
| 14 | 95 | 95 | 100 | 75 | 100 | 100 |
| 15 | 90 | 100 | 75 | 65 | 15 | 80 |
| 16 | 5 | 5 | 0 | 20 | 0 | 5 |

The above preferred embodiments and examples are given to illustrate the scope and spirit of the present invention. These preferred embodiments and examples will make apparent, to those skilled in the art, other embodiments and examples. These other embodiments and examples are within the contemplation of the subject invention. Therefore, the scope of the present invention should be limited only by the appended claims.

What is claimed is:

1. A compound having the structural formula

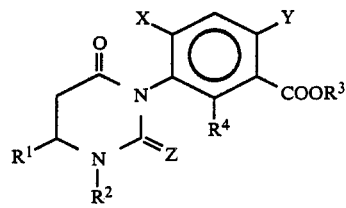

where $R^1$ is hydrogen, $C_1$-$C_4$ alkyl, $C_3$-$C_6$ cycloalkyl, $C_3$-$C_4$ alkenyl or trifluoromethyl; $R^2$ is $C_1$-$C_4$ alkyl, $C_3$-$C_6$ cycloalkyl, $C_3$-$C_4$ alkenyl, $C_7$-$C_{10}$ aralkyl or $C_7$-$C_{10}$ haloaralkyl; $R^3$ is hydrogen or $C_1$-$C_4$ alkyl; $R^4$ is hydrogen or $C_1$-$C_2$ alkyl; X is halogen; Y is hydrogen; $C_1$-$C_4$ alkyl or halogen; and Z is oxygen or sulfur.

2. A compound in accordance with claim 1 where $R^1$ is hydrogen, $C_1$-$C_2$ alkyl or trifluoromethyl; $R^2$ is $C_1$-$C_3$ alkyl, cyclohexyl, propenyl, $C_7$-$C_9$ aralkyl or $C_7$-$C_9$ haloaralkyl; $R^3$ is hydrogen or $C_1$-$C_3$ alkyl; $R^4$ is hydrogen or methyl; X is fluorine; Y is hydrogen, $C_1$-$C_2$ alkyl or chlorine; and Z is oxygen.

3. A compound in accordance with claim 2 wherein $R^1$ is hydrogen, methyl or trifluoromethyl; $R^2$ is methyl, isopropyl, cyclohexyl, propenyl or chlorobenzyl; $R^3$ is hydrogen or isopropyl; $R^4$ is hydrogen; and Y is methyl or chlorine.

4. A herbicidal composition comprising a herbicidally effective amount of the compound of claim 1 and a suitable carrier therefor.

5. A herbicidal composition comprising a herbicidally effective amount of the compound of claim 2 and a suitable carrier therefor.

6. A herbicidal composition comprising a herbicidally effective amount of the compound of claim 3 and a suitable carrier therefor.

7. A method for controlling weeds comprising applying a herbicidally effective amount of the compound of claim 1 to the locus to be protected.

8. A method for controlling weeds comprising applying a herbicidally effective amount of the compound of claim 2 to the locus to be protected.

9. A method for controlling weeds comprising applying a herbicidally effective amount of the compound of claim 3 to the locus to be protected.

* * * * *